US00PP18697P2

(12) United States Plant Patent
Bernuetz

(10) Patent No.: US PP18,697 P2
(45) Date of Patent: Apr. 1, 2008

(54) ***ARGYRANTHEMUM* PLANT NAMED 'BONMADCINK'**

(50) Latin Name: ***Argyranthemum* ×*hybrida***
Varietal Denomination: Bonmadcink

(75) Inventor: Andrew Bernuetz, Silverdale (AU)

(73) Assignee: Bonza Botanicals Pty., Ltd., Sydney (AU)

( * ) Notice: Subject to any disclaimer, the term of this patent is extended or adjusted under 35 U.S.C. 154(b) by 0 days.

(21) Appl. No.: 11/601,542

(22) Filed: Nov. 17, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—June Hwu
(74) *Attorney, Agent, or Firm*—Audrey Charles

(57) ABSTRACT

A new and distinct cultivar of *Argyranthemum* plant named 'Bonmadcink', characterized by its medium pink-colored flowers, medium green-colored foliage; and moderately vigorous, compact, and upright-mounded growth habit.

1 Drawing Sheet

Latin name genus and species of plant claimed: *Argyranthemum×hybrida.*
Variety denomination: 'Bonmadcink'.

BACKGROUND OF THE INVENTION

The present invention relates to a new and distinct cultivar of *Argyranthemum* plant botanically known as *Argyranthemum×hybrida* and hereinafter referred to by the cultivar name 'Bonmadcink'.

The new cultivar originated in a controlled breeding program in Yellow Rock, New South Wales, Australia during January 2002. The objective of the breeding program was the development of *Argyranthemum* cultivars that are freely flowering with unique flower coloration and a freely branching, compact, and upright growth habit.

The new *Argyranthemum* cultivar is the result of cross-pollination. The female (seed) parent of the new cultivar is the proprietary *Argyranthemum×hybrida* breeding selection designated 01-157, not patented, characterized by its double type medium pink-colored flowers, medium green-colored foliage, and compact-mounded growth habit. The male (pollen) parent of the new cultivar is Bright Carmine 'Supalight' U.S. Plant Pat. No. 14,128, characterized by its single type dark pink-colored flowers, medium green-colored foliage, and upright growth habit. The new cultivar was discovered and selected as a single flowering plant within the progeny of the above stated cross-pollination during May 2003 in a controlled environment at Yellow Rock, New South Wales.

Asexual reproduction of the new cultivar by terminal stem cuttings since May 2003 at Yellow Rock New South Wales, Australia and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Bonmadcink' as a new and distinct cultivar of *Argyranthemum* plant:

1. Medium pink-colored flowers;
2. Medium green-colored foliage; and
3. Moderately vigorous, compact, and upright-mounded growth habit.

Plants of the new cultivar differ from plants of the female parent primarily in flower form and from plants of the male parent primarily in flower form, flower color, and growth habit.

Of the many commercially available *Argyranthemum* cultivars known to the inventor, the most similar in comparison to the new cultivar is MADEIRA Double Pink 'OHAR1245', U.S. Plant Pat. No. 16,283. However, in side by side comparisons, plants of the new cultivar differ from plants of 'OHAR01245' in the following characteristics:

1. Plants of the new cultivar are shorter than plants of 'OHAR01245'; and
2. Plants of the new cultivar have smaller leaves than plants of 'OHAR01245'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Bonmadcink'. The plants were grown in 4.5 inch pots for 7 weeks in a greenhouse at West Chicago, Ill.

DETAILED BOTANICAL DESCRIPTION

Figure 1:
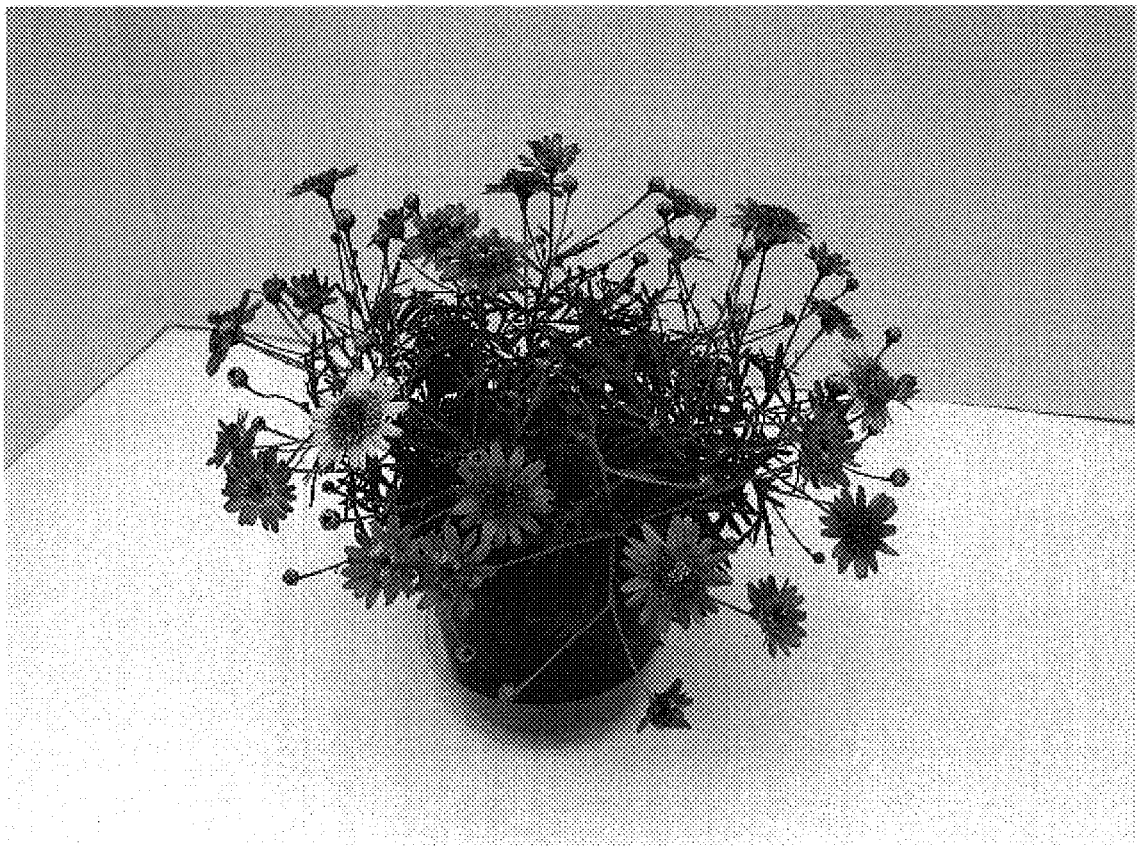
FIG. 1 illustrates a side view of the overall growth and flowering habit of 'Bonmadcink'.
Figure 2:
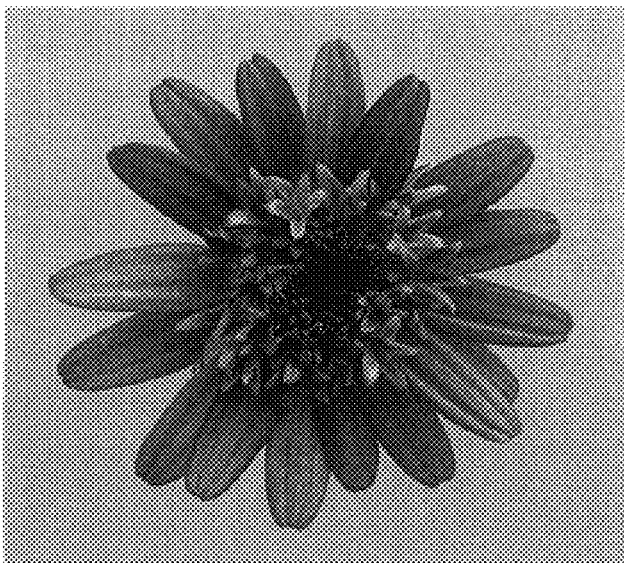
FIG. 2 illustrates a close-up view of an individual inflorescence of 'Bonmadcink'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on May 11, 2006, 2006 between 9:00 a.m. and 11:00 a.m. under natural light conditions in West Chicago, Ill.

The following descriptions and measurements describe plants produced from cuttings taken from stock plants and grown in a glass-covered greenhouse under conditions comparable to those used in commercial practice. The plants were grown at West Chicago, Ill. in 4.5 inch pots for 7 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day.

Botanical classification: *Argyranthemum×hybrida* cultivar Bonmadcink.

Parentage:

*Female parent.*—*Argyranthemum×hybrida* breeding selection designated 01-157, not patented.

*Male parent.*—Bright Carmine 'Supalight' U.S. Plant Pat. No. 14,128.

Propagation:

*Type cutting.*—Terminal stem.

*Time to initiate roots.*—Approximately 6 to 8 days.

*Time to produce a rooted cutting.*—Approximately 21 to 28 days.

*Root description.*—Fibrous.

*Rooting habit.*—Freely branching.

Plant description:

*Crop time.*—Approximately 6 to 9 weeks from a rooted cutting.

*Growth habit and general appearance.*—Moderately vigorous, compact, and upright-mounded.

*Size.*—Height from soil level to top of plant plane: Approximately 13.9 cm. Width: Approximately 28.1 cm.

*Branching habit.*—Freely branching. Quantity of main branches per plant: Approximately 12.

*Branch.*—Strength: Strong. Length from soil level to base of peduncle: Approximately 8.0 cm. Diameter: Approximately 4.1 mm. Length of central internode: Approximately 8.5 mm. Texture: Glabrous. Color of young stem: Glaucous, 144C. Color of mature stem: Glaucous, 144C with woody base of 199B.

Foliage description:

*General description.*—Quantity of leaves per main branch: Approximately 11. Fragrance: Slight. Form: Simple. Arrangement: Alternate.

*Leaves.*—Aspect: Acute angle to stem; leaf blade perpendicular to stem with age. Shape: Obovate. Margin: parted. Apex: Acute, cuspidate. Base: Attenuate, decurrent. Venation pattern: Pinnate. Length of mature leaf: Approximately 6.0 cm. Width of mature leaf: Approximately 3.3 cm. Texture of upper and lower surfaces: Glabrous with sparsely pubescent midvein. Color of upper surface of young foliage: Glaucous, 137A with venation of 137B. Color of lower surface of young foliage: 138A with venation of 138B. Color of upper surface of mature foliage: Glaucous, 137A with venation of 137D. Color of lower surface of mature foliage: 137C with venation of 137D.

Flowering description:

*Flowering habit.*—'Bonmadcink' is freely flowering under outdoor growing conditions with substantially continuous blooming from spring through autumn and year-round in greenhouse environment.

*Lastingness of individual inflorescence on the plant.*—Approximately 15 to 16 days.

Inflorescence description:

General description. —Type: Solitary, composite. Persistent. Shape: Round. Aspect: Facing upward and outward. Arrangement: Terminal, positioned above the foliage. Disc and ray florets develop acropetally on a capitulum. Average quantity per plant: Approximately 25. Diameter: Approximately 3.2 cm. Fragrance: None.

*Peduncle.*—Strength: Strong, pliable. Aspect: Erect. Length: Approximately 6.8 cm. Diameter: Approximately 2.0 mm. Texture: Sparsely pubescent. Color: 138B.

*Bud.*—Rate of opening: Generally takes 7 to 8 days for bud to progress from first color to fully open flower. Average quantity per plant: Approximately 19.

*Bud just before opening.*—Shape: Ovoid. Diameter: Approximately 6.6 mm. Color: 72B.

*Ray florets.*—Quantity per inflorescence: Approximately 18. Arrangement: Imbricate in a single whorl. Aspect: Slightly convex, turning downward with age. Shape: Ligulate. Margin: Entire. Apex: Emarginate with 3 tips. Base: Attenuate, fused to form a tube. Length: Approximately 1.4 cm. Width: Approximately 4.5 mm. Texture of upper surface: Glabrous. Texture of lower surface: Glabrous, ribbed. Color of upper surface when first open: 72B. Color of lower surface when first open: 70B. Color of upper surface when fully open: N80D with an overlay of N78B. Color of lower surface when fully open: N81D.

*Disc florets.*—Quantity per inflorescence: Approximately 114. Arrangement: Massed in center of inflorescence. Shape: Tubular with 5 lobes. Margin: Entire. Apex: Acute. Base: Truncate. Length: Approximately 7.6 mm. Diameter at apex: Approximately 2.4 mm. Diameter at base: Approximately 1 mm. Texture: Glabrous with glandular pubescence on lower half. Gland color: Colorless. Color when fully open: N80A at tips transitioning to 155B toward base of N144C.

*Disc.*—Diameter: Approximately 1.8 cm. Depth: Approximately 5.5 mm.

*Receptacle.*—Shape: Cone. Height: Approximately 3.0 mm. Diameter at base: Approximately 3.0 mm. Color: N144D.

*Phyllaries.*—Quantity per inflorescence Approximately 29. Arrangement: Imbricate, in several whorls. Shape: Lanceolate. Margin: Entire. Apex: Acute. Base: Truncate. Length: Approximately 4.6 mm. Width: Approximately 2.4 mm. Texture of upper and lower surfaces: Glabrous, papery along edges. Color of upper surface: 143A in with transparent margins of N199B. Color of lower surface: Closest to 143C in center with transparent margins of N199B.

*Reproductive organs.*—Androecium: Present on disc florets only. Stamen quantity: 5 per floret. Stamen length: Approximately 3.0 mm. Anther shape: Linear. Anther length: Approximately 1.0 mm. Anther color: 15A. Pollen amount: None observed. Gynoecium: Present on ray and disc florets. Pistil quantity: 1 per floret. Pistil length: Approximately 5.0 mm. Stigma shape: Two-parted. Stigma length: Less than 1 mm. Stigma color: 6A. Style length: Approximately 4.0 mm. Style color: 145C. Ovary length: Approximately 1.0 mm. Ovary color: 145D.

Seed and fruit production: Neither seed nor fruit production has been observed.

Disease and pest resistance: Resistance to pathogens and pests common to *Argyranthemum* has not been observed.

What is claimed is:

1. A new and distinct cultivar of *Argyranthemum* plant named 'Bonmadcink', substantially as herein shown and described.

* * * * *